United States Patent [19]

Dougherty et al.

[11] Patent Number: 5,368,819
[45] Date of Patent: Nov. 29, 1994

[54] AUTOMATED PROCESS CHLORIDE ANALYZER

[75] Inventors: Wm. Richard Dougherty; Donald J. Skahan, both of Drexel Hill, Pa.

[73] Assignee: Arco Chemical Technology, L.P., Wilmington, Del.

[21] Appl. No.: 76,620

[22] Filed: Jun. 14, 1993

Related U.S. Application Data

[62] Division of Ser. No. 794,278, Nov. 19, 1991, Pat. No. 5,260,220.

[51] Int. Cl.$^5$ .......................................... G01N 33/00
[52] U.S. Cl. .................................... 422/68.1; 422/62; 422/75; 422/101; 436/124; 436/125; 436/126; 436/51; 436/139; 436/163; 436/175; 436/177; 436/181
[58] Field of Search .................. 422/62, 63, 67, 68.1, 422/75, 101; 436/124, 125, 126, 50, 51, 139, 141, 163, 175, 177, 178, 181

[56] References Cited

U.S. PATENT DOCUMENTS

| | | | |
|---|---|---|---|
| 3,351,635 | 11/1967 | Kollar | 549/529 |
| 3,660,035 | 5/1972 | Marsh | 436/60 |
| 4,434,233 | 2/1984 | Bzdula | 436/60 |
| 4,650,768 | 3/1987 | Cahill et al. | 436/125 |
| 4,808,299 | 2/1989 | Latimer et al. | 208/251 R |
| 4,942,133 | 7/1990 | Pauly et al. | 436/124 X |
| 5,013,667 | 5/1991 | Lynn et al. | 436/126 |
| 5,122,236 | 6/1992 | Smith, Jr. et al. | 203/43 |
| 5,192,509 | 3/1993 | Surjaatmadja et al. | 422/75 |

FOREIGN PATENT DOCUMENTS 1007315 10/1965 United Kingdom .

OTHER PUBLICATIONS

Soviet Inventions Illustrated, Derwent Publications, abstract of SU 938,103, Jun. 25, 1982.

*Primary Examiner*—James C. Housel
*Assistant Examiner*—Maureen M. Wallenhorst
*Attorney, Agent, or Firm*—William C. Long

[57] ABSTRACT

An automated analysis system is provided for the determination of impurities in a liquified hydrocarbon stream. The system employs a hydrocarbon capture vessel for capturing a hydrocarbon sample, a water scrubbing vessel for extracting impurities from the hydrocarbon sample and a titration zone for analyzing the amount of impurities in the aqueous extract.

3 Claims, 3 Drawing Sheets

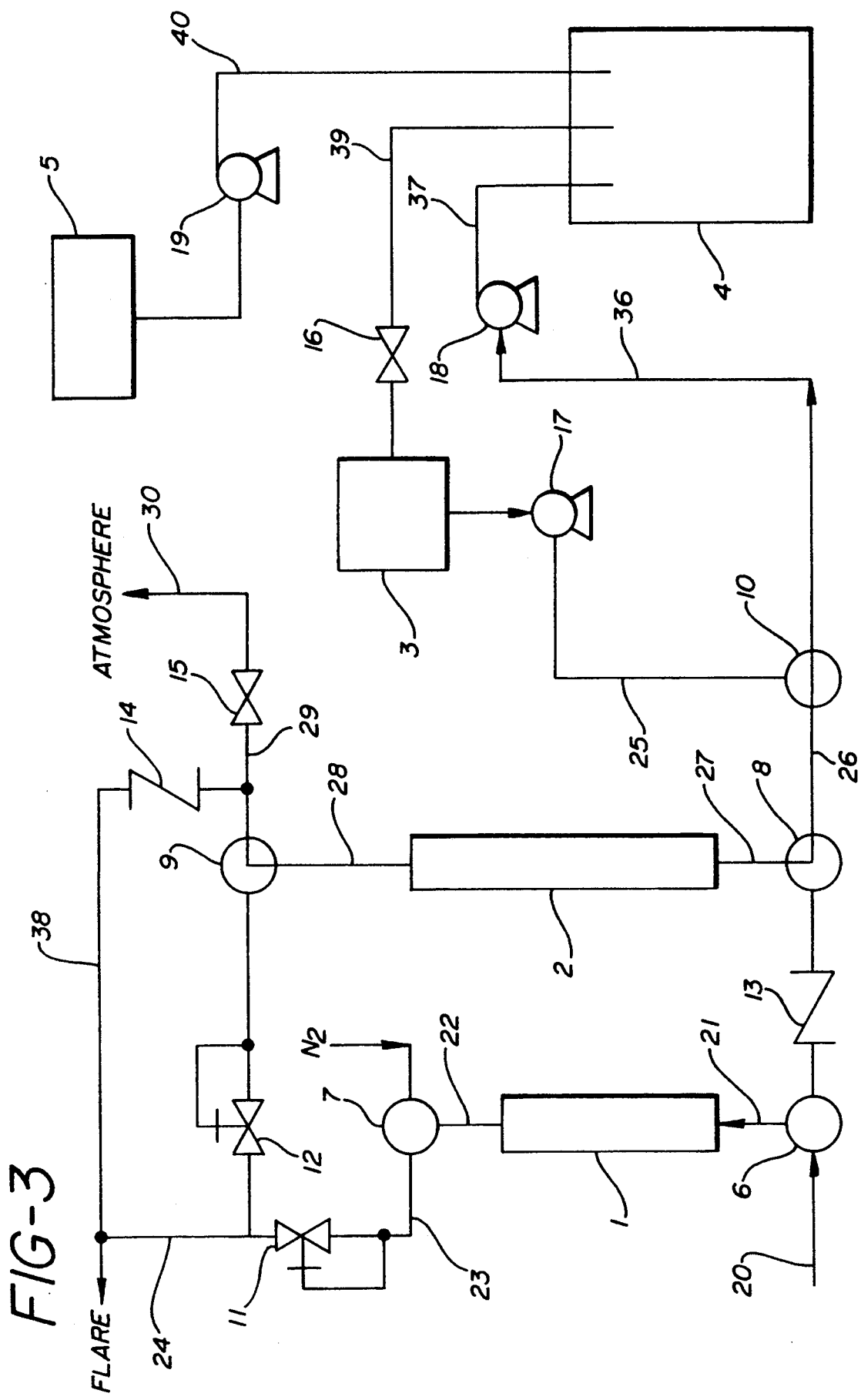

AUTOMATED PROCESS CHLORIDE ANALYZER

This is a divisional of Ser. No. 07/794,278 filed on Nov. 19, 1991, now U.S. Pat. No. 5,260,220, issued November 1993.

BACKGROUND OF THE INVENTION

1. Field of the Invention

The present invention relates to a method and apparatus for the automated analysis of chemical plant process streams and in particular to a method and apparatus for the automated analysis of a liquified hydrocarbon stream such as isobutane feed to a propylene oxide/tertiary butyl alcohol plant to monitor the inorganic chloride content of the hydrocarbon feed.

2. Description of the Prior Art

In many industrial chemical plant processes, problems arise as a result of the presence of chloride or chlorine containing compounds in hydrocarbon feed streams. For example, isobutane is an essential feed stream to commercial plants which co-produce propylene oxide (PO) and tertiary butyl alcohol (TBA) by procedures described, for example, in U.S. Pat. No. 3,351,635. Experience has shown that the inorganic chloride content of the feed isobutane can fluctuate rapidly and widely in commercial practice. The introduction of chlorides such as iron chloride to a PO/TBA plant can cause serious problems including chloride stress cracking of stainless steel components, leakage and plant shutdown.

Current techniques for monitoring the chloride content of hydrocarbon feed streams such as isobutane involve manually obtaining feed samples under conditions of elevated pressure, transport of the samples to a testing laboratory where the samples are manually extracted by an aqueous wash and then titrated with silver nitrate for chloride content. Although such techniques are quite accurate, they are labor intensive and are unable to produce results quick enough so that prompt measures can be taken to prevent contamination of the plant.

U.S. Pat. No. 4,942,133 provides a procedure for the continuous analysis of the chloride ion content of overhead waters downstream of a hydrocarbon distillation column, but this does not relate to automated chloride analysis of hydrocarbon feed to a chemical plant.

U.S. Pat. NO. 4,650,768 relates to automated methods for determination of chloride in an aqueous fluid sample, but this does not relate to automated chloride analysis of hydrocarbon feed to a chemical plant.

SUMMARY OF THE INVENTION

In accordance with the present invention, an automated sampling method and system has been developed for the effective monitoring of the amount of chloride in plant hydrocarbon feed streams such as the isobutane feed to a PO/TBA plant. The automated system comprises in combination an apparatus for capturing a liquid hydrocarbon sample for analysis, an apparatus for aqueous extraction of inorganic chlorides from the captured sample, and an apparatus to titrate the aqueous extract for chloride content together with means for sequentially transferring various streams among the apparatus. Through practice of the invention, representative samples from a heterogeneous hydrocarbon stream can be obtained, sampling frequency can be increased and the time required for analysis can be decreased.

DESCRIPTION OF THE DRAWING

The attached drawings, FIGS. 1-3, illustrate schematically the automated sampling system of the invention and the operation thereof.

FIG. 1 illustrates the first step in the automated sequence where the hydrocarbon sample is captured in vessel 1 and deionized water is charged to vessel 2;

FIG. 2 illustrates the second step in the automated sequence where the captured hydrocarbon sample is transferred to scrubbing vessel 2 and impurities are water extracted from the hydrocarbon;

FIG. 3 illustrates the third step where hydrocarbon is vaporized from vessel 2 and where the aqueous phase containing extracted impurities is transferred and titrated in zone 4.

DETAILED DESCRIPTION OF THE INVENTION

Figure 1:
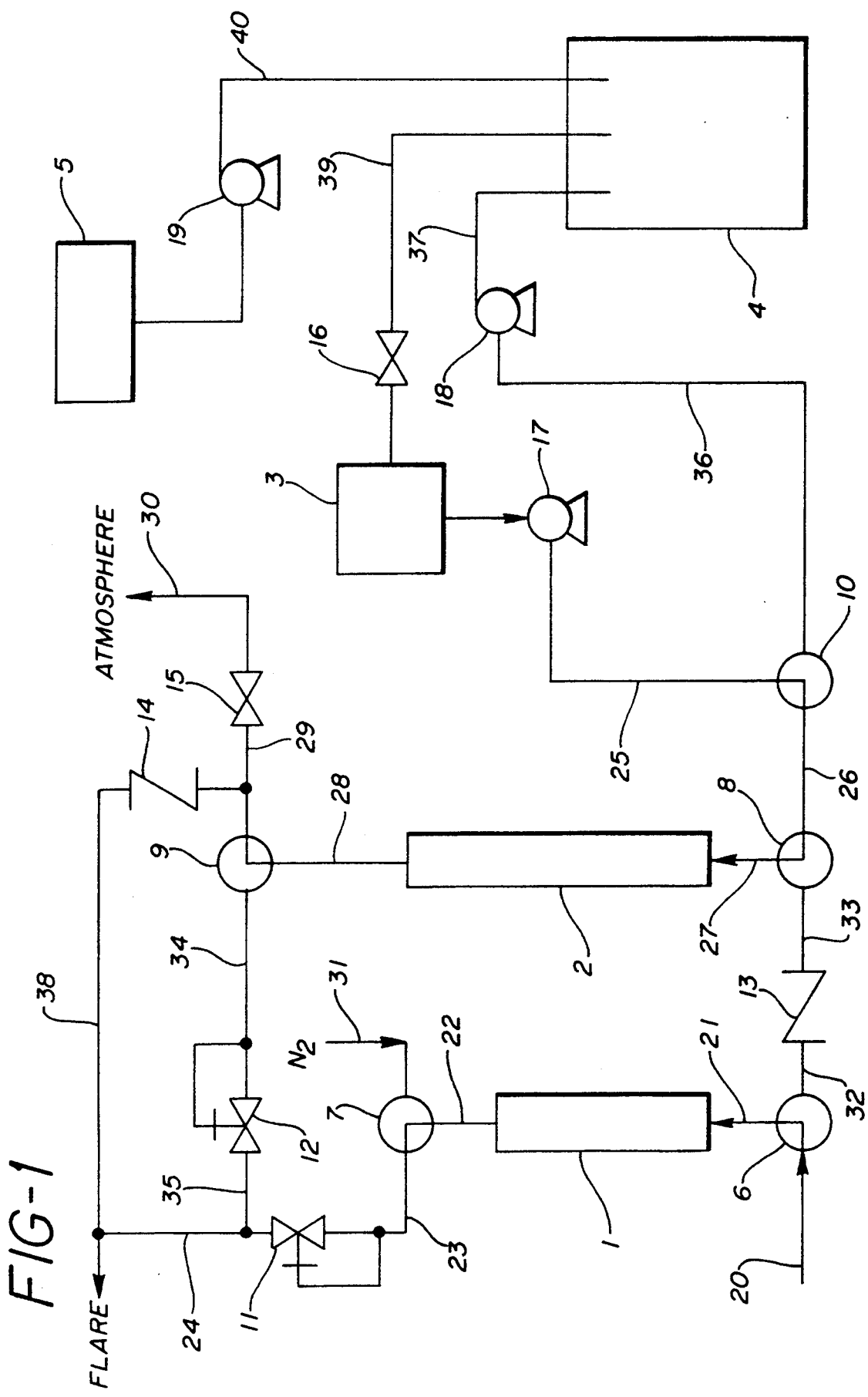

The present invention can be applied to the automated analysis of hydrocarbons which are normally a gas and which can be readily liquified. In particular, hydrocarbons having 2 to 5 carbon atoms are suitably analyzed in accordance with the invention; examples of such hydrocarbons are ethylene, ethane, propylene, propane, n-butane, isobutane, the butylenes, the pentanes and the pentenes.

In preferred practice, the automated analysis system functions to determine the chloride content of the hydrocarbon. However, the system is readily adapted to the determination of other impurities such as sulfur and the like in the feed.

In order to more clearly describe the automated analysis system of the invention and its operation, reference is made to the attached drawings which illustrate a preferred system and the operation thereof.

Referring to the drawings, the same automated system is shown in each of the three drawings. Each drawing represents a separate step in the automated analysis sequence and shows the valve positioning and flows of the various steams as the automated analysis sequence is carried out.

In all of the drawings, vessel 1 represents a sample capture vessel, vessel 2 represents a water scrubbing vessel, vessel 3 represents a deionized water reservoir vessel, vessel 4 represents a conventional titration zone, vessel 5 represents a standard solution-containing vessel, valves 6, 7, 8, 9 and 10 are conventional valves functioning to direct a fluid stream to either of two conduits, valves 11 and 12 are conventional pressure regulating valves and valves 13, 14, 15 and 16 are conventional valves which can be opened or closed to regulate fluid flow. Pumps 17, and 19 are provided to accomplish liquid transfer.

Step 1 of the automated analysis sequence is illustrated in FIG. 1 in connection with the analysis of isobutane for chloride content. At the initiation of the analysis sequence, a stream of liquid isobutane at elevated pressure sufficient to maintain the isobutane in liquid state, e.g. 100 psig, is diverted from the plant feed line and passes via line 20 to valve 6 and thence via line 21 to sample collection vessel 1. Sample collection vessel 1 is made of an appropriate material such as stainless steel and has a measured capacity, e.g. 500 cc. Liquid isobutane fills collection vessel 1, with excess isobutane passing via line 22 to valve 7 and then via line 23 to pressure regulating valve 11 and then finally via line 24 to flare. Pressure regulating valve 11 maintains a sufficient back-pressure on vessel 1, e.g. 80 psig, to maintain the isobutane in the liquid phase therein.

In the automated analysis sequence, at the same time that isobutane is being captured in vessel 1, a measured amount of deionized water, e.g. 50 cc., is pumped from zone 3 via pump 17 and lines 25, 26 and 27 through valves 10 and 8 to scrubbing vessel 2. While the deionized water is being charged to scrubbing vessel 2, this vessel is vented to the atmosphere via line 28, valve 9, line 29, valve 15 and line 30.

Figure 2:
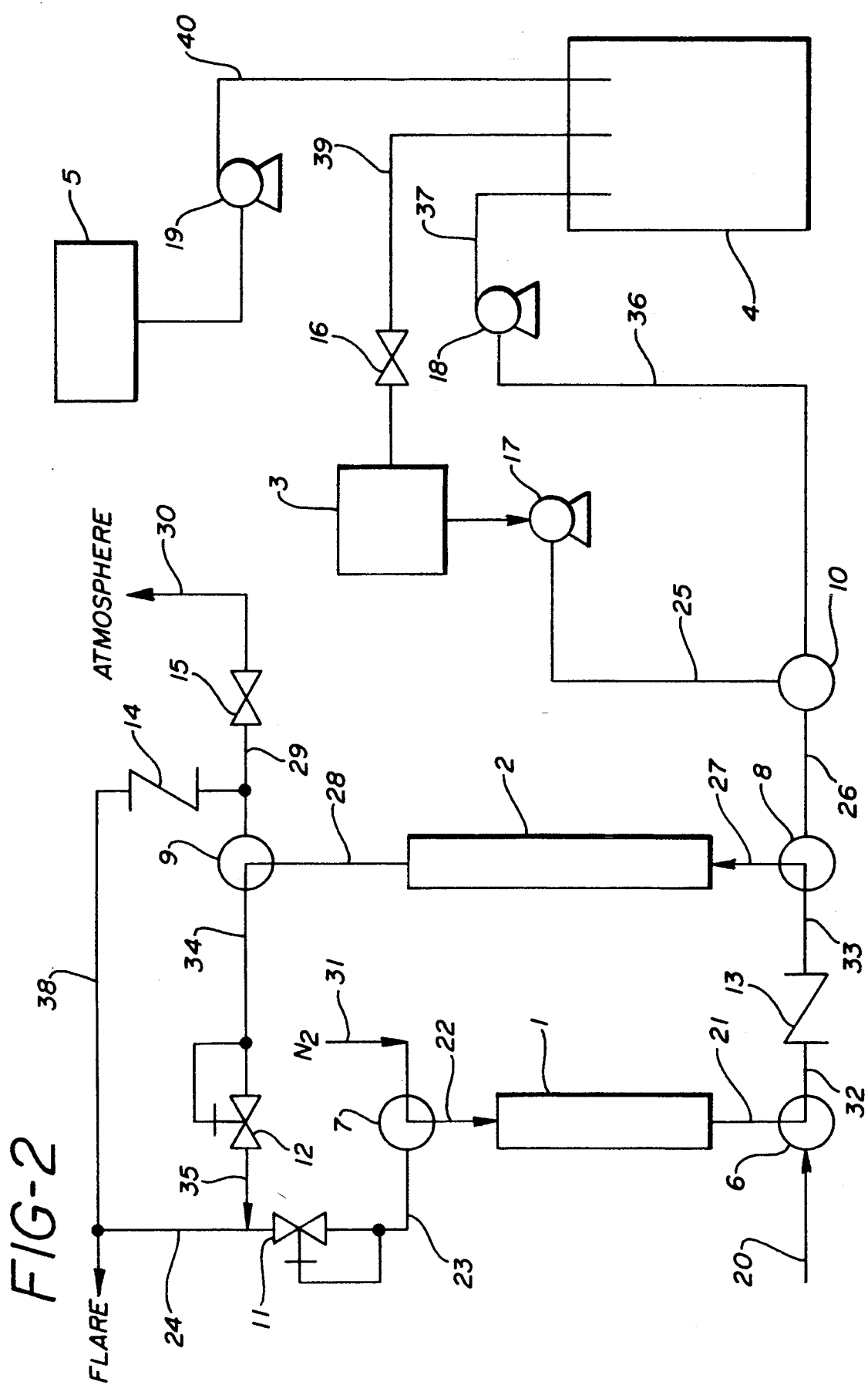

When a suitable amount of liquid isobutane has been charged to capture vessel 1 and water to scrubbing vessel 2, the automated analysis system proceeds to step 2 which is illustrated in FIG. 2. Nitrogen at elevated pressure, e.g. at 80 psig, is provided to capture vessel 1 via line 31, valve 7 and line 22. This nitrogen forces the liquid isobutane from vessel 1 via line 21, valve 6, line 32, valve 13, line 33, valve 8 and line 27 into scrubbing vessel 2.

In scrubbing vessel 2, the liquid isobutane passes upwardly in intimate contact with the previously charged deionized water due to the density differences between the fluids. As a result of this intimate contact, the chloride compounds contained in the liquid isobutane sample are extracted from the isobutane into the deionized water phase. Because the volumes of isobutane and deionized water are fixed, the impurities extracted from the isobutane are concentrated by a known factor in the deionized water.

The isobutane passes upwardly through scrubbing vessel 2 with excess exiting via line 28, valve 9, line 34, pressure regulating valve 12, line 35 and line 24 to the flare. Pressure regulating valve 12 maintains sufficient pressure, for example 40 psig, to ensure that liquid-liquid extraction contact occurs in scrubbing vessel 2 between the isobutane and the deionized water.

At the completion of the extraction step, the automated analysis system proceeds to step 3 which is illustrated in FIG. 3. The pressure in vessel 2 is reduced to allow isobutane to evaporate from vessel 2. Check valve 14 is set at lower pressure, e.g. 3 psig, to allow the great bulk of the isobutane to pass as vapor to flare via line 28, valve 9, check valve 14 and line 38. Appropriately, scrubbing vessel 2 is provided with a source of heat, for example a heat tape, to prevent freezing of the deionized water as the isobutane evaporates. When the pressure in scrubbing vessel 2 equilibrates with that of check valve 14, valve 15 opens to atmosphere to allow complete depressurization of the scrubbing vessel and removal of the remaining very small amount of isobutane.

After the scrubbing vessel 2 is vented to atmospheric pressure via line 28, valve 9, line 29, valve 15 and line 30, the aqueous phase from scrubbing vessel 2 is transferred via 27, valve 8, line 26, valve 10, line 36, pump 18, and line 37 to titrator 4. In titrator 4, the aqueous phase containing chloride extracted from the isobutane is titrated using known methods and equipment in order to determine the chloride content of the aqueous extract. A suitable and preferred titrating apparatus is a Tytronics Incorporated process titrator such as the Tytronics FPA 300 TM Series employing standard silver nitrate titration methods. Such apparatus is fully automated and capable of receiving the aqueous extract sample, titrating with silver nitrate and reporting chloride content of the sample. Results of the titration are immediately transferred to the process control room, thus providing a convenient and accurate measure of the chloride content of the isobutane feed stream sample.

The titration in titrator 4 is carried out in accordance with known procedures. Basically, a known volume of the chloride-containing sample from the scrubbing vessel is titrated with a standard aqueous silver nitrate solution and the potential between a silver electrode and a non-chloride-containing reference electrode is continuously measured. Chloride in the sample being titrated forms silver chloride with the titrating solution and immediately precipitates. When all the chloride in the sample being analyzed has reacted, the presence of silver ions in the sample is detected by the sharp potential increase. The silver nitrate titrating solution, e.g. an 0.01 molar aqueous solution, is added at a known and constant rate so that the time before appearance of silver ions can be determined and automatically compared with the time for appearance of silver ions in a standard calibrating solution for which the chloride content is known. By the ratio of these times, the chloride content of the sample, and thus of the hydrocarbon, is directly determined.

A suitable cycle for the automated analysis system is a 15-minute cycle, that is, every 15 minutes the analysis process described above is repeated. Through this frequent and accurate analytical procedure, steps can quickly be taken when excessive quantities of chlorine or chloride compound are detected in the feed isobutane, thus preventing significant corrosion problems downstream.

Additional features of the present invention provide that after each titration, deionized water passes from vessel 3 through valve 16 and via line 39 to titrator 4 in order to thoroughly wash and clean the titration apparatus.

A further feature is that at periodic intervals preferably once a day, the system auto-calibrates by means of a standard solution passed from vessel 5 via pump 19 and line 40 to titrator 4 in order to ensure accuracy of the operation.

The opening and closing of the various valves to accomplish the analysis sequence described above is done automatically by conventional procedures according to the programmed cycle.

The automated analysis system of the present invention provides a sturdy and durable apparatus which is capable of a high degree of accuracy in the analysis of liquified hydrocarbons for impurities such as chlorine and chloride compounds. The apparatus requires only low maintenance and has been demonstrated to be extremely accurate and reliable.

We claim:

1. An automated analysis system comprising a hydrocarbon capture vessel, conduit means for passing a predetermined sample amount of liquified hydrocarbon to said capture vessel, a water scrubbing vessel adapted to extract water soluble impurities from the liquified hydrocarbon sample, conduit means for passing a predetermined amount of deionized water to said scrubbing vessel, conduit means located between the capture vessel and the scrubbing vessel for transferring the predetermined sample amount of liquified hydrocarbon to the water containing scrubbing vessel so as to place the liquified hydrocarbon sample into contact with water contained therein and to produce a deionized water extract containing the water soluble impurities from the liquified hydrocarbon sample, titration means for analyzing the deionized water extract to determine the amount of impurities extracted from said liquified hydrocarbon sample, pressure reducing means for reducing pressure in said water scrubbing vessel to a level at which liquified hydrocarbon contained thereon vaporizes, conduit means for the removal and discard of hydrocarbon vapor from the scrubbing vessel, and conduit means located between the scrubbing vessel and the titration means for passing the deionized water extract from the scrubbing vessel to the titration means.

2. The automated analysis system of claim 1 wherein the titration means for analyzing the deionized water extract is an automated titrating apparatus.

3. The automated analysis system of claim 2 wherein means are provided for the periodic auto-calibration of the titration means.

* * * * *